(12) United States Patent
Melsheimer et al.

(10) Patent No.: US 8,002,729 B2
(45) Date of Patent: Aug. 23, 2011

(54) MULTI-LUMEN CATHETER ASSEMBLY

(75) Inventors: Jeffry S. Melsheimer, Springville, IN (US); Christopher D. Bosel, Bloomington, IN (US); Drew P. Lyons, Ellettsville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 585 days.

(21) Appl. No.: 11/842,330

(22) Filed: Aug. 21, 2007

(65) Prior Publication Data

US 2009/0054824 A1    Feb. 26, 2009

(51) Int. Cl.
*A61M 37/00* (2006.01)
*A61M 31/00* (2006.01)

(52) U.S. Cl. ............... 604/6.16; 604/4.01; 604/5.01; 604/508

(58) Field of Classification Search ............ 604/4.05, 604/5.01, 5.04, 6.16, 508, 509
See application file for complete search history.

(56) References Cited

U.S. PATENT DOCUMENTS

| | | | |
|---|---|---|---|
| 3,938,530 A | 2/1976 | Santomieri | 128/349 R |
| 3,946,741 A | 3/1976 | Adair | 128/347 |
| 4,129,129 A | 12/1978 | Amrine | 128/214 R |
| 4,134,402 A | 1/1979 | Mahurkar | 128/214 R |
| 4,154,242 A | 5/1979 | Termanini | 128/349 R |
| 4,431,426 A | 2/1984 | Groshong et al. | 604/280 |
| 4,493,696 A | 1/1985 | Uldall | 604/43 |
| RE31,855 E | 3/1985 | Osborne | 604/161 |
| 4,568,329 A | 2/1986 | Mahurkar | 604/43 |
| 4,581,025 A | 4/1986 | Timmermans | 604/264 |
| 4,583,968 A | 4/1986 | Mahurkar | 604/43 |
| 4,643,711 A | 2/1987 | Bates | 604/4 |
| 4,655,745 A | 4/1987 | Corbett | 604/49 |
| 4,680,029 A | 7/1987 | Ranford et al. | 604/280 |
| 4,692,141 A | 9/1987 | Mahurkar | 604/43 |
| 4,733,669 A | 3/1988 | Segal | 128/663 |
| 4,769,005 A | 9/1988 | Ginsburg et al. | 604/53 |
| 4,772,268 A | 9/1988 | Bates | 604/174 |
| 4,808,163 A | 2/1989 | Laub | 604/105 |
| 4,878,893 A | 11/1989 | Chin | 604/21 |
| 4,904,238 A | 2/1990 | Williams | 604/43 |
| 4,936,826 A | 6/1990 | Amarasinghe | 604/52 |
| 4,973,301 A | 11/1990 | Nissenkorn | 604/8 |
| 4,995,865 A | 2/1991 | Gahara et al. | 604/43 |
| 4,995,868 A | 2/1991 | Brazier | 604/105 |

(Continued)

FOREIGN PATENT DOCUMENTS

EP    0 301 854 A2    2/1989

(Continued)

*Primary Examiner* — Leslie R Deak

(74) *Attorney, Agent, or Firm* — Brinks Hofer Gilson & Lione

(57) ABSTRACT

A multi-lumen catheter assembly for use in the extracorporeal treatment of a body fluid of a patient. The catheter assembly includes an elongated catheter body having a pair of lumens extending therethrough, and a septum separating the lumens. The catheter body has an aspiration port in communication with a first lumen for transporting fluid withdrawn from a body vessel to a treatment unit, and an infusion port in communication with a second lumen for return of treated fluid to the vessel. The infusion port is positioned distal of the aspiration port along a length of the catheter body. A flexible member is provided, wherein the flexible member has an end receivable in the first lumen and another end engaged with the catheter body distal of the aspiration port. The flexible member is structured and arranged to maintain a spacing between the aspiration port and a wall of the vessel.

16 Claims, 7 Drawing Sheets

U.S. PATENT DOCUMENTS

| | | | | |
|---|---|---|---|---|
| 5,106,368 | A | 4/1992 | Uldall et al. | 604/43 |
| 5,156,597 | A | 10/1992 | Verreet et al. | 604/175 |
| 5,193,533 | A | 3/1993 | Body et al. | 128/207.14 |
| 5,221,256 | A | 6/1993 | Mahurkar | 604/43 |
| 5,250,034 | A | 10/1993 | Appling et al. | 604/164 |
| 5,275,610 | A | 1/1994 | Eberbach | 606/198 |
| 5,352,198 | A | 10/1994 | Goldenberg et al. | 604/95 |
| 5,360,397 | A | 11/1994 | Pinchuk | 604/27 |
| 5,364,344 | A | 11/1994 | Beattie et al. | 604/43 |
| 5,403,291 | A | 4/1995 | Abrahamson | 604/280 |
| 5,409,460 | A | 4/1995 | Krumme | 604/107 |
| 5,443,449 | A | 8/1995 | Buelna | 604/105 |
| 5,486,159 | A | 1/1996 | Mahurkar | 604/4 |
| 5,489,278 | A | 2/1996 | Abrahamson | 604/280 |
| 5,509,897 | A | 4/1996 | Twardowski et al. | 604/43 |
| 5,509,900 | A * | 4/1996 | Kirkman | 604/104 |
| 5,514,112 | A | 5/1996 | Chu et al. | 604/267 |
| 5,518,498 | A | 5/1996 | Lindenberg et al. | 600/30 |
| 5,522,400 | A | 6/1996 | Williams | 128/772 |
| 5,549,245 | A | 8/1996 | Kish | 238/283 |
| 5,571,093 | A | 11/1996 | Cruz et al. | 604/270 |
| 5,681,280 | A | 10/1997 | Rusk et al. | 604/95 |
| 5,702,365 | A * | 12/1997 | King | 604/105 |
| 5,713,853 | A | 2/1998 | Clark et al. | 604/53 |
| 5,749,826 | A | 5/1998 | Faulkner | 600/29 |
| 5,817,067 | A | 10/1998 | Tsukada | 604/256 |
| 5,840,067 | A * | 11/1998 | Berguer et al. | 604/104 |
| 5,857,464 | A | 1/1999 | Desai | 128/658 |
| 5,885,258 | A | 3/1999 | Sachdeva et al. | 604/281 |
| 5,888,196 | A | 3/1999 | Bonutti | 600/204 |
| 5,957,900 | A | 9/1999 | Ouchi | 604/264 |
| 6,001,079 | A | 12/1999 | Pourchez | 604/43 |
| 6,033,397 | A | 3/2000 | Laufer et al. | 606/27 |
| 6,052,612 | A | 4/2000 | Desai | 600/435 |
| 6,071,263 | A | 6/2000 | Kirkman | 604/104 |
| 6,177,049 | B1 | 1/2001 | Schnell et al. | 422/44 |
| 6,179,813 | B1 | 1/2001 | Ballow et al. | 604/164 |
| 6,238,412 | B1 | 5/2001 | Dubrul et al. | 606/200 |
| 6,270,490 | B1 | 8/2001 | Hahnen | 604/509 |
| 6,283,940 | B1 | 9/2001 | Mulholland | 604/96.01 |
| 6,293,958 | B1 | 9/2001 | Berry et al. | 606/191 |
| 6,336,933 | B1 | 1/2002 | Parodi | 606/139 |
| 6,409,700 | B1 | 6/2002 | Siegel, Jr. et al. | 604/43 |
| 6,454,775 | B1 * | 9/2002 | Demarais et al. | 606/128 |
| 6,461,321 | B1 | 10/2002 | Quinn | 604/43 |
| 6,475,207 | B1 | 11/2002 | Maginot et al. | 604/508 |
| 6,482,169 | B1 | 11/2002 | Kuhle | 604/6.16 |
| 6,517,529 | B1 | 2/2003 | Quinn | 604/528 |
| 6,527,737 | B2 | 3/2003 | Kaneshige | 604/48 |
| 6,547,761 | B2 | 4/2003 | Liu | 604/104 |
| 6,558,349 | B1 | 5/2003 | Kirkman | 604/104 |
| 6,558,350 | B1 | 5/2003 | Hart et al. | 604/104 |
| 6,569,150 | B2 | 5/2003 | Teague et al. | 604/524 |
| 6,579,261 | B1 | 6/2003 | Kawamura | 604/105 |
| 6,579,302 | B2 | 6/2003 | Duerig et al. | 606/198 |
| 6,767,339 | B2 | 7/2004 | Reydel | 604/175 |
| 6,858,001 | B1 | 2/2005 | Aboul-Hosn | 600/16 |
| 6,939,327 | B2 | 9/2005 | Hall et al. | |
| 6,966,886 | B2 | 11/2005 | Appling | 604/6.16 |
| 7,001,354 | B2 | 2/2006 | Suzuki et al. | 604/6.11 |
| 2001/0011182 | A1 | 8/2001 | Dubrul et al. | 606/200 |
| 2001/0018576 | A1 | 8/2001 | Quinn | 604/264 |
| 2001/0041858 | A1 | 11/2001 | Ray et al. | 604/93.01 |
| 2002/0026156 | A1 | 2/2002 | Quinn | 604/264 |
| 2002/0072768 | A1 | 6/2002 | Ginn | 606/213 |
| 2002/0107506 | A1 | 8/2002 | McGuckin, Jr. et al. | 604/523 |
| 2002/0143292 | A1 | 10/2002 | Flinchbaugh | 604/107 |
| 2002/0177822 | A1 | 11/2002 | St. Cyr et al. | 604/264 |
| 2003/0032918 | A1 | 2/2003 | Quinn | 604/43 |
| 2003/0093029 | A1 | 5/2003 | McGuckin, Jr. et al. | 604/43 |
| 2003/0139763 | A1 | 7/2003 | Duerig et al. | 606/198 |
| 2004/0049157 | A1 | 3/2004 | Plishka et al. | 604/164.09 |
| 2004/0210180 | A1 | 10/2004 | Altman | 604/4.01 |
| 2005/0033264 | A1 | 2/2005 | Redinger | 604/523 |
| 2005/0148929 | A1 | 7/2005 | Gingles | 604/95.04 |
| 2005/0177094 | A1 | 8/2005 | Igarashi et al. | 604/43 |
| 2005/0261663 | A1 | 11/2005 | Patterson et al. | |
| 2006/0004325 | A1 | 1/2006 | Hamatake et al. | 604/43 |
| 2006/0253063 | A1 | 11/2006 | Schweikert | 604/30 |
| 2007/0016124 | A1 | 1/2007 | McGraw | 604/4.01 |

FOREIGN PATENT DOCUMENTS

| | | |
|---|---|---|
| WO | WO 01/019425 A1 | 3/2001 |
| WO | WO 02/064202 A3 | 8/2002 |
| WO | WO 03/066125 A | 8/2003 |
| WO | WO 2005/049125 A1 | 6/2005 |
| WO | WO 2006/002192 A2 | 1/2006 |

* cited by examiner

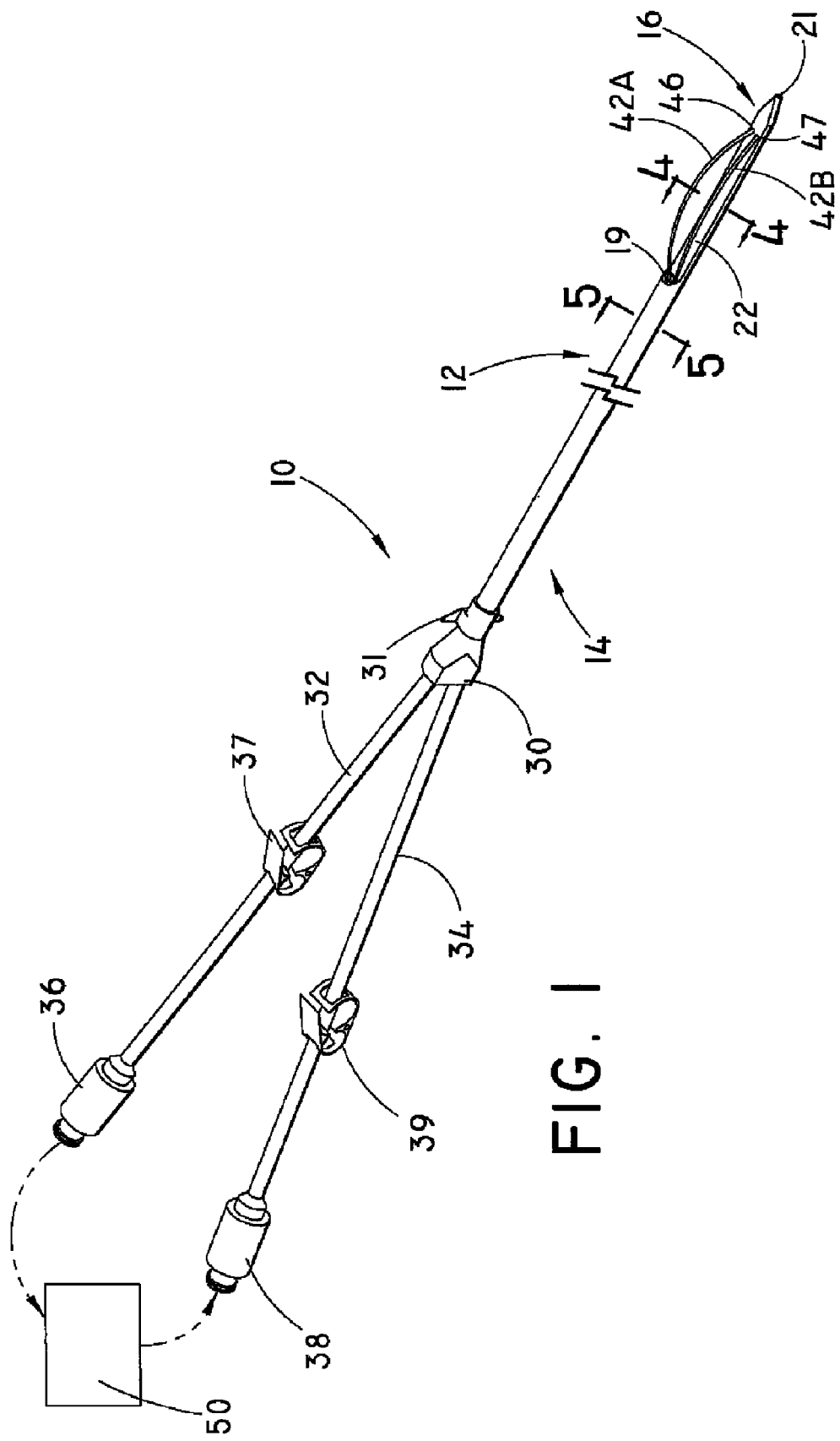
FIG. I

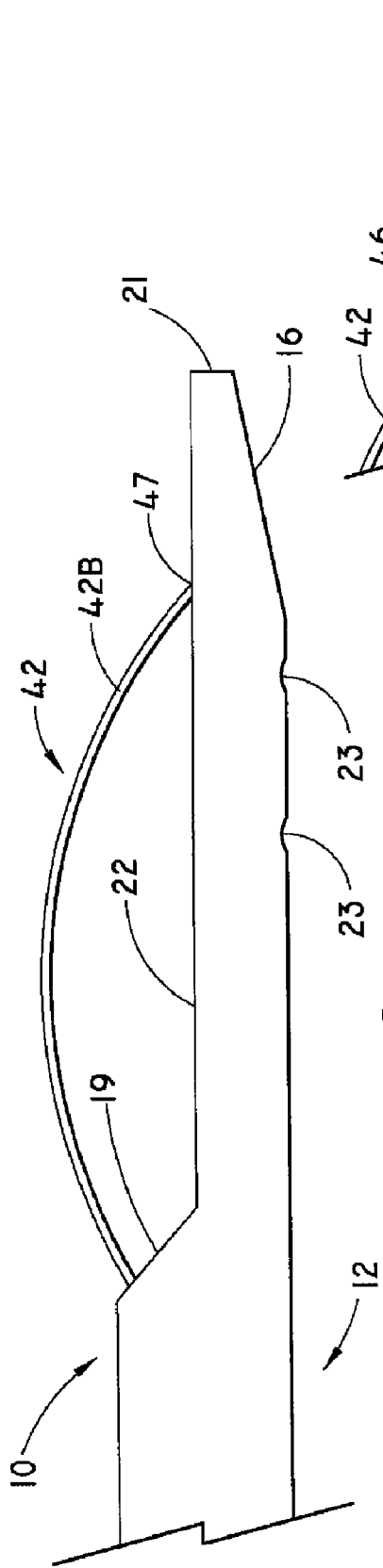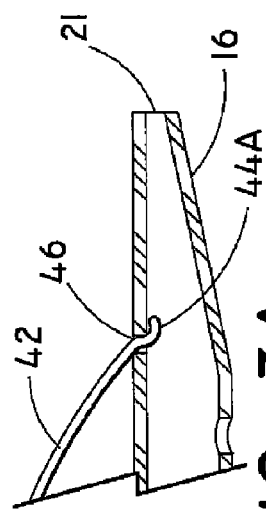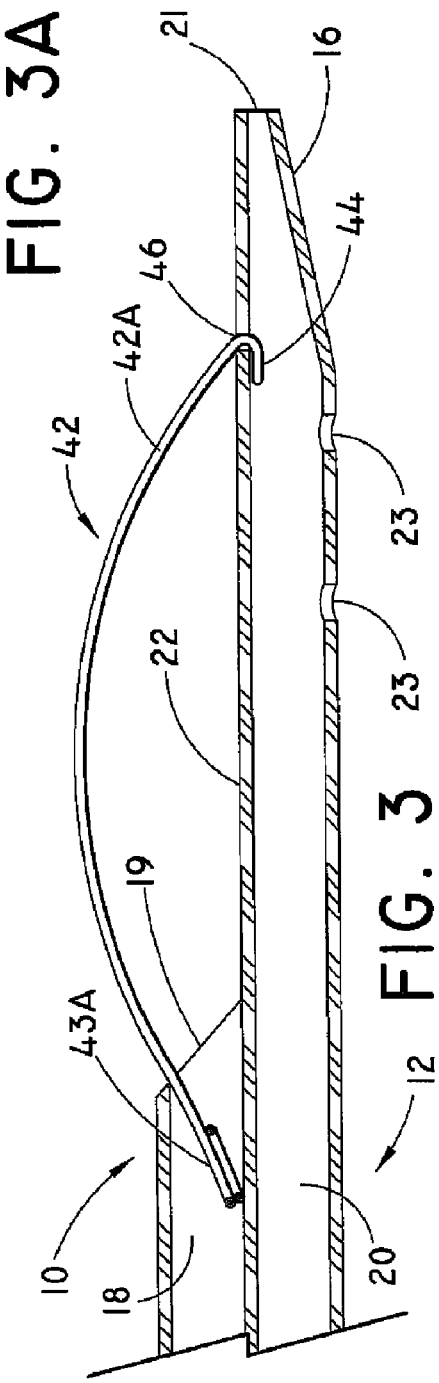

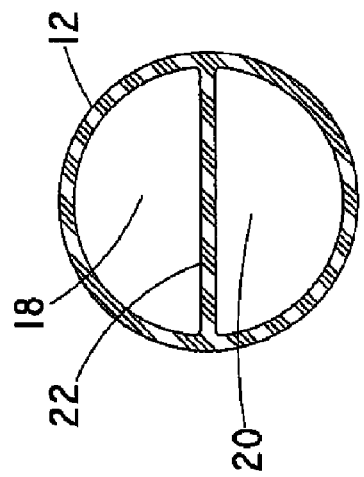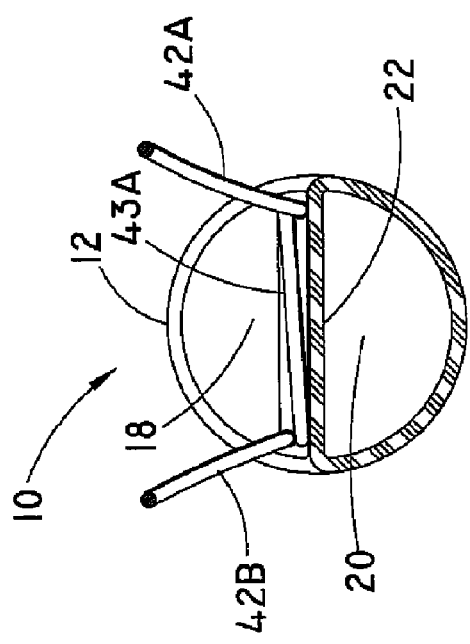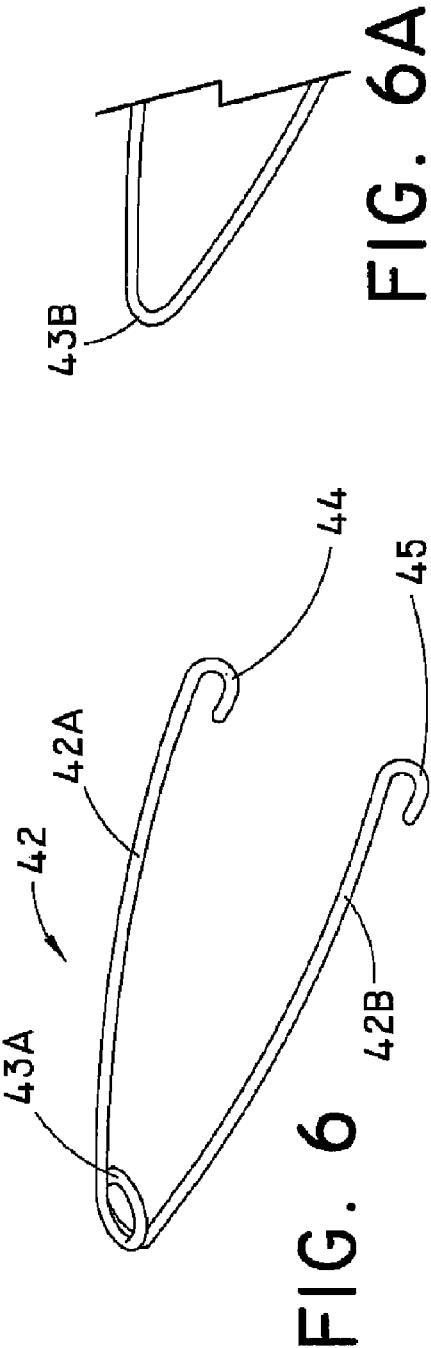

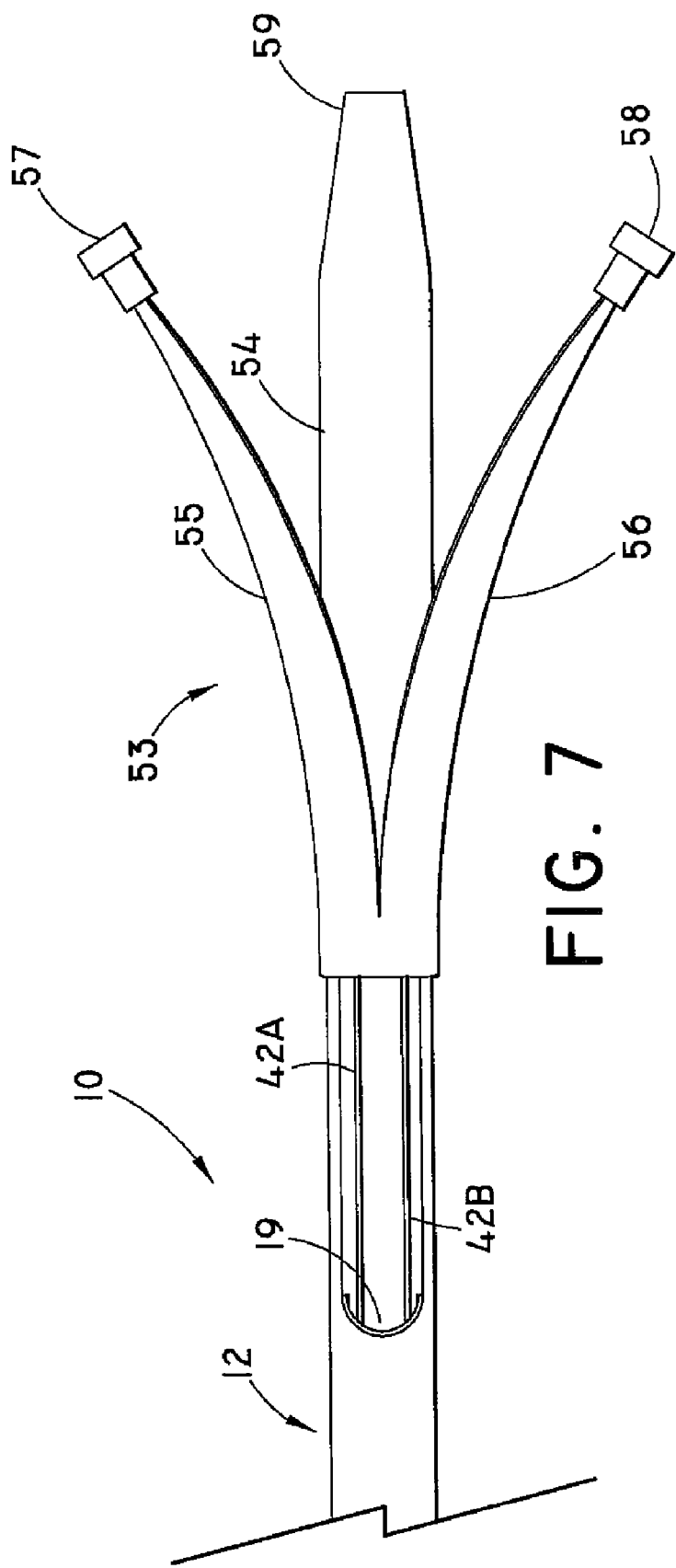

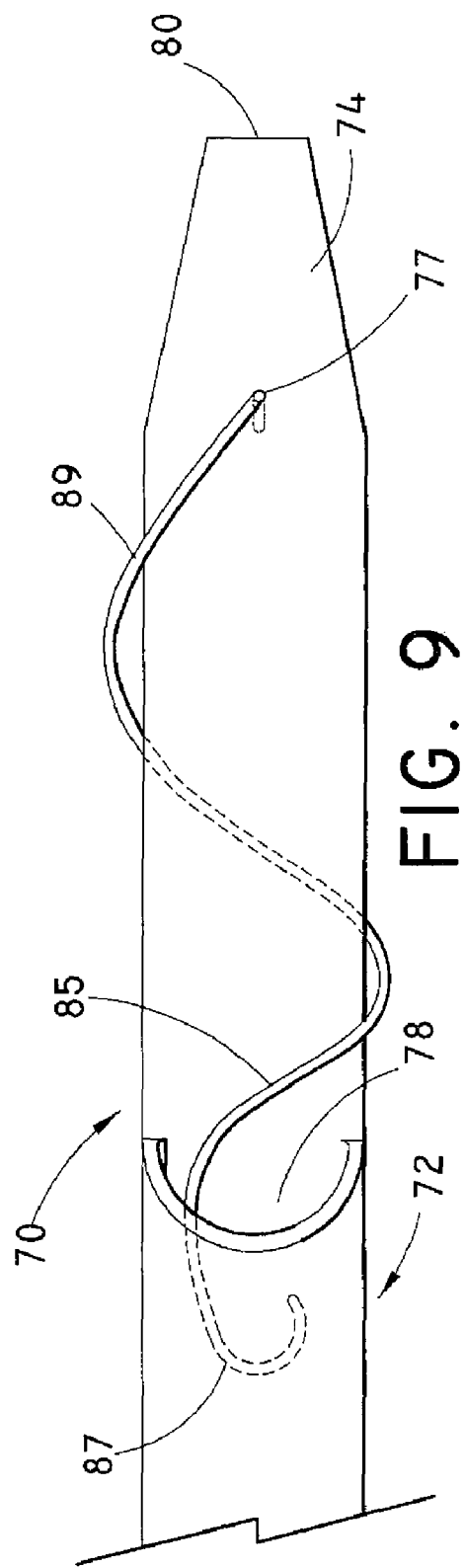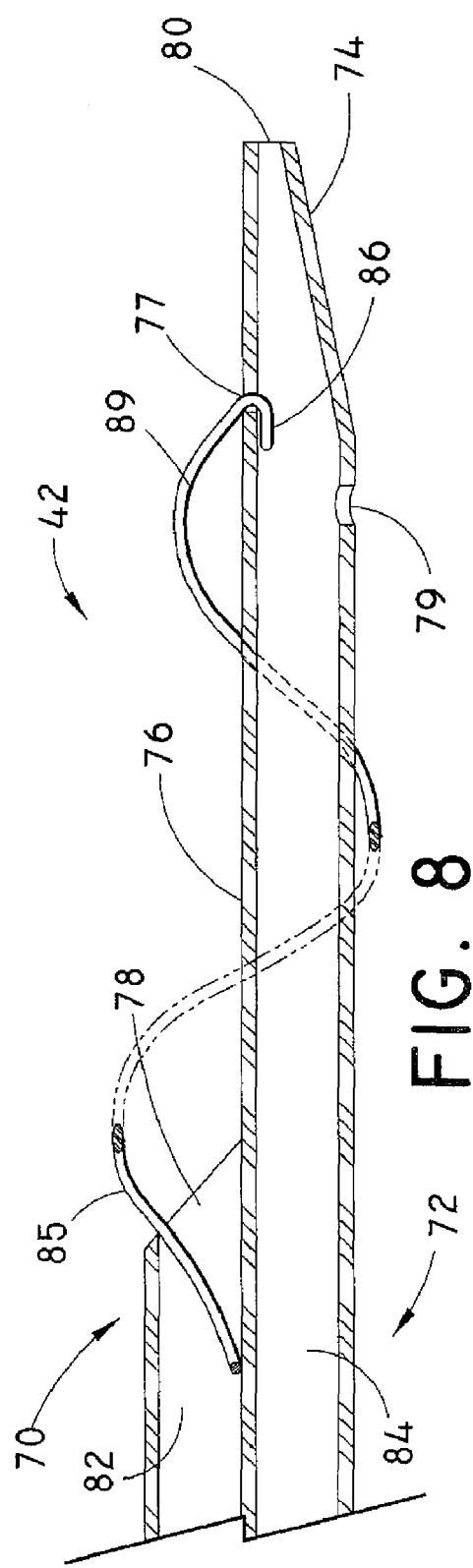

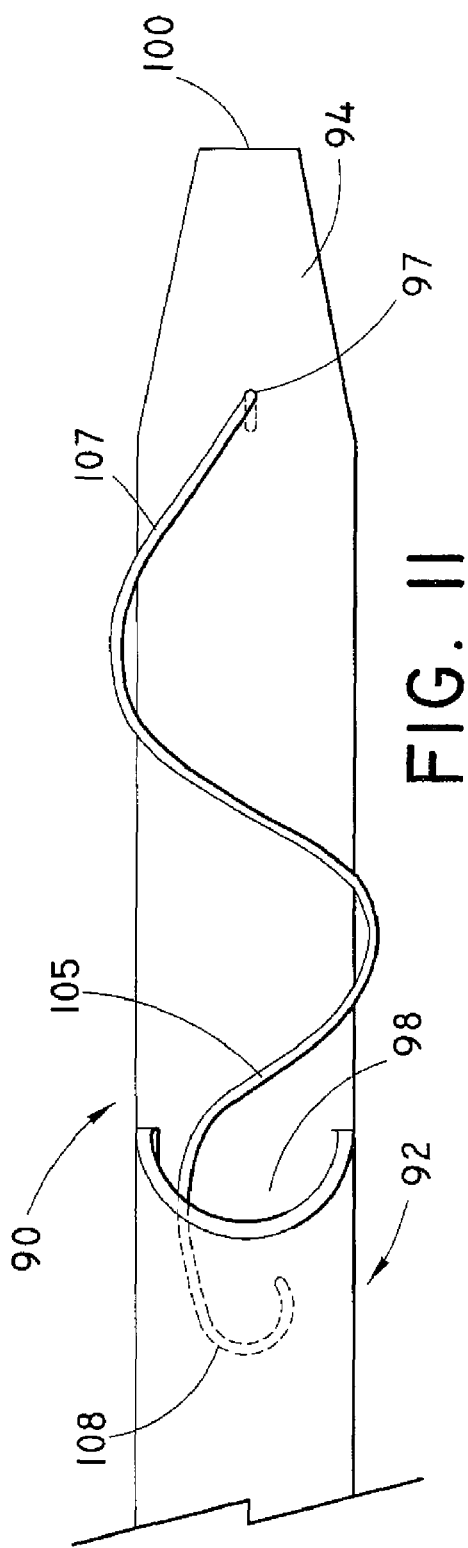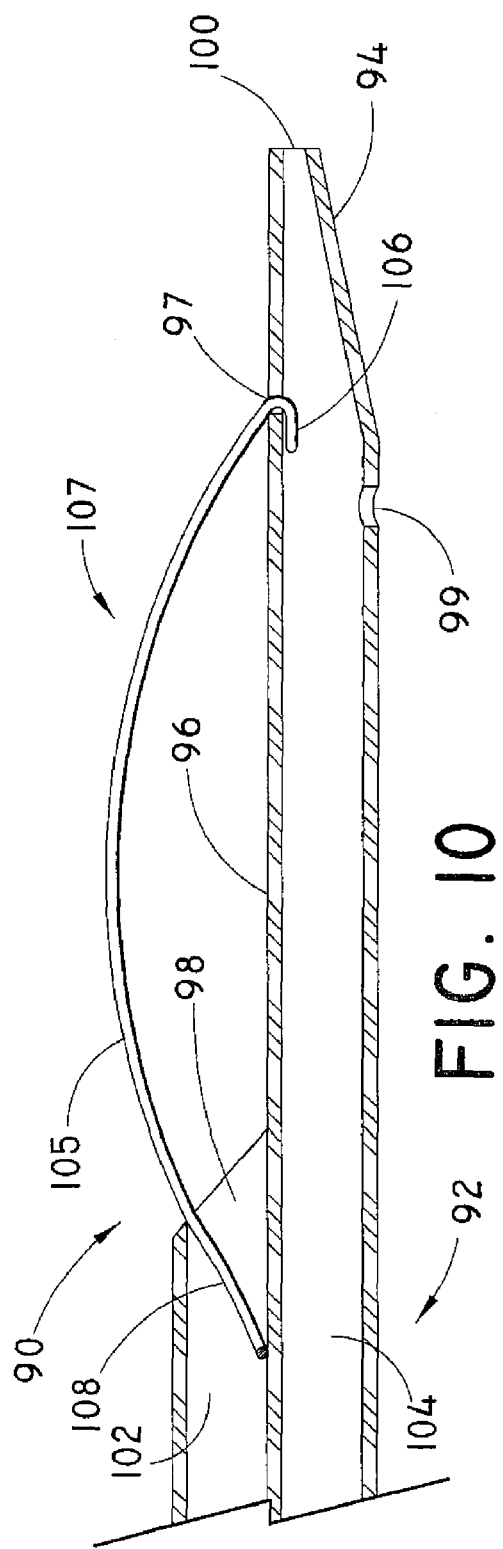

MULTI-LUMEN CATHETER ASSEMBLY

BACKGROUND

Technical Field

The present application relates generally to a catheter for use in transporting fluids, and more particularly, to a multi-lumen catheter assembly for transporting fluids from the patient's body for extracorporeal treatment, and returning the treated fluids to the body.

Multi-lumen catheters are commonly used for transporting bodily fluids during an extracorporeal treatment process for the bodily fluid. A fluid is withdrawn from the body through one of the lumens, generally referred to as the aspiration, or withdrawal, lumen. The fluid is subjected to a treatment process, and thereafter returned to the body through the other lumen, generally referred to as the infusion, or return, lumen.

In many cases, the extracorporeal treatment involves a hemodialysis procedure. During hemodialysis, blood is withdrawn from a blood vessel through the aspiration lumen and routed to a dialyzer for treatment. The cleansed blood is then returned to the vessel through the infusion lumen. When such a catheter is used for hemodialysis, whether for acute (short-term, generally thirty days or less) or longer term hemodialysis, it is generally inserted into the body through either the internal jugular vein, subclavian vein or femoral vein. In addition to hemodialysis, extracorporeal catheters can also be used for other procedures, such as pheresis and hemofiltration, in which a fluid is removed from the body for treatment and later returned to the body.

A variety of hemodialysis catheters are commercially available. Among the types of commercially available catheters are: 1) a dual lumen catheter wherein one lumen (e.g., the blood infusion lumen) terminates distal to the other lumen (e.g., the blood aspiration lumen) Some catheters of this type are provided with a midline split (e.g., the Uldall catheter), while others do not have such a split (e.g., the COOK® DDS catheter); 2) catheters having a slitted valve in the distal tip that acts as a pressure valve opening. This valve opens inwardly for blood aspiration, outwardly for blood infusion, and remains closed when not in use (e.g., the Groshong catheter); 3) cuffed central venous silicone catheters that are tunneled underneath the skin to reduce infection (e.g., Broviac, Leonard and Hickman catheters); 4) dual lumen catheters having a tapered tip and two adjacent holes communicating with one lumen just proximal to the tip to assist with outflow, and two adjacent holes communicating with the other lumen (180 degrees removed) just proximal to the first set of holes to assist with inflow (e.g., the Mahurkar catheter); 5) dual lumen catheters having a diverting structure consisting of a shoulder that has a straight up distal face and a sloped proximal face to reduce access recirculation and raise pressure in the vicinity of the inlet aperture (U.S. Pat. No. 6,409,700); and 6) catheters designed for femoral approach having two sets of staggered side ports, resulting in a total of four side ports.

One problem with existing multi-lumen catheters is that such catheters can experience decreased flow rates over time. Decreased flow rates may be caused by, among other things, blockage of the aspiration and/or infusion ports in the catheter. Various factors can cause a port to become blocked. One common cause of port blockage is the inadvertent positioning of one or more ports of the catheter against the vessel wall. This positioning hinders the free flow of fluid through the obstructed port, and in some cases, prevents fluid flow altogether. Another common cause of port blockage is the formation of fibrin sheaths along the ports. Fibrin sheaths may be formed, e.g., in response to the vessel wall washing effect or clotting.

Decreased, or restricted, flow is clearly undesirable in a multi-lumen for use in extracorporeal treatment of a fluid, such as a hemodialysis catheter. In order for the extracorporeal fluid treatment to be effective, fluid flow through the catheter must not be restricted in any appreciable way. Thus, it is important to position existing catheters in a manner such that fluid flow is not restricted. Additionally, it is important to insure that all ports are unobstructed.

Various attempts have been made in the art to reduce port blockage. For example, as described above, some catheters are provided with side ports at various locations on the catheter. Side ports generally provide some reduction in port blockage, however such ports themselves are subject to blockage when placed against the vessel wall, or as a result of fibrin formation on the port. Other attempts have been made to reduce port blockage by providing the staggered side-by-side dual lumen design described above, wherein the respective aspiration and infusion tubes are of different lengths so that the ports aspirate and infuse the bodily fluid at different axial locations of the catheter While this arrangement may avoid some problems involved in maintaining adequate flow through the lumens, such catheters can still be subject to suboptimal flow. Some catheters, such as the Mahurkar catheter described above, must be rotated if inflow is blocked because the catheter is up against the vein wall. Although each of these techniques may be at least partially effective in reducing some types of blockage, reduced flow rate continues to be a problem in the art.

It is desired to provide a multi-lumen catheter assembly for use in the extracorporeal treatment of bodily fluids, wherein the multi-lumen catheter assembly is structured in a manner to minimize port blockage, and to provide for optimal fluid flow through the lumens of the catheter.

SUMMARY

The present invention addresses the shortcomings in the prior art. In one form thereof, the invention comprises a multi-lumen catheter assembly. The multi-lumen catheter assembly comprises a catheter body having a plurality of lumens extending therein, the lumens being separated in the catheter body by a septum. The catheter body has an aspiration port in communication with a first lumen for transporting fluid withdrawn from a body vessel, and an infusion port in communication with a second lumen for return of fluid to the vessel. The infusion port is positioned distal of the aspiration port along a length of the catheter body. A flexible member is provided, wherein the flexible member has an end receivable in the first lumen and another end engaged with the catheter body distal of the aspiration port. The flexible member is structured and arranged to maintain a spacing between the aspiration port and a wall of the vessel.

In another form thereof, the invention comprises a multi-lumen catheter assembly for use in the extracorporeal treatment of a body fluid of a patient. An elongated catheter body has a proximal end, a distal end, a pair of lumens extending therethrough, and a septum separating the lumens. The distal end tapers to open distal tip. One of the lumens comprises an aspiration lumen, and the other lumen comprises an infusion lumen. An aspiration port is in communication with the aspiration lumen for receiving the body fluid from a body vessel of the patient for transport to a treatment unit. The open distal end comprises an infusion port in communication with the infusion lumen for returning treated body fluid to the vessel.

A flexible wire member has an end receivable in the aspiration lumen and has another end fixed to an attachment point at the septum distal to the aspiration port. The end of the flexible wire member receivable in the aspiration lumen is movable within the lumen such that a profile of the flexible wire member is selectively movable between a first position wherein the flexible wire member has a radial profile sufficient to maintain a spacing between the aspiration port and a wall of the vessel, and a second position wherein the radial profile does not substantially exceed an outer diameter of the elongated catheter body.

In yet another form thereof, the invention comprises a multi-lumen catheter assembly comprising a catheter body having a plurality of lumens extending therein, and a septum separating the first and second lumens. The catheter body has an aspiration port in communication with a first lumen for transporting fluid withdrawn from a body vessel, and an infusion port in communication with a second lumen for return of fluid to the vessel. The infusion port is positioned distal of the aspiration port along a length of the catheter body. A centering member is provided having a proximal portion disposed along the length of the catheter member proximal of the aspiration port, and having a flexible member extending from the proximal portion distal of the aspiration port along the catheter length. The flexible member is configured to maintain a spacing between the aspiration port and a wall of the body vessel.

BRIEF DESCRIPTION OF THE DRAWINGS

FIG. 1 is a perspective view of a catheter assembly according to one embodiment of the present invention;

FIG. 2 is an enlarged side view of the distal portion of the catheter assembly of FIG. 1;

FIG. 3 is a longitudinal sectional view of the portion of the catheter assembly shown in FIG. 2;

FIG. 3A is a longitudinal sectional view similar to that of FIG. 3, wherein a toggle is substituted for the hook of FIG. 3;

FIG. 4 is a transverse sectional view of the catheter assembly of FIG. 1 taken along line 4-4;

FIG. 5 is a transverse sectional view of the catheter assembly of FIG. 1 taken along line 5-5;

FIG. 6 is a view of the double bail prior to insertion into the catheter body;

FIG. 6A is a variation of the double bail of FIG. 6;

FIG. 7 is a top view of the distal end of the catheter assembly, wherein an introducer is provided for reducing the profile of the double bail;

FIG. 8 is a side sectional view of the distal portion of another embodiment of a catheter assembly according to the present invention;

FIG. 9 is a top view of the catheter assembly of FIG. 8;

FIG. 10 is a side sectional view of the distal portion of still another embodiment of a catheter assembly according to the present invention;

FIG. 11 is a top view of the catheter assembly of FIG. 10;

DETAILED DESCRIPTION

Figure 12:
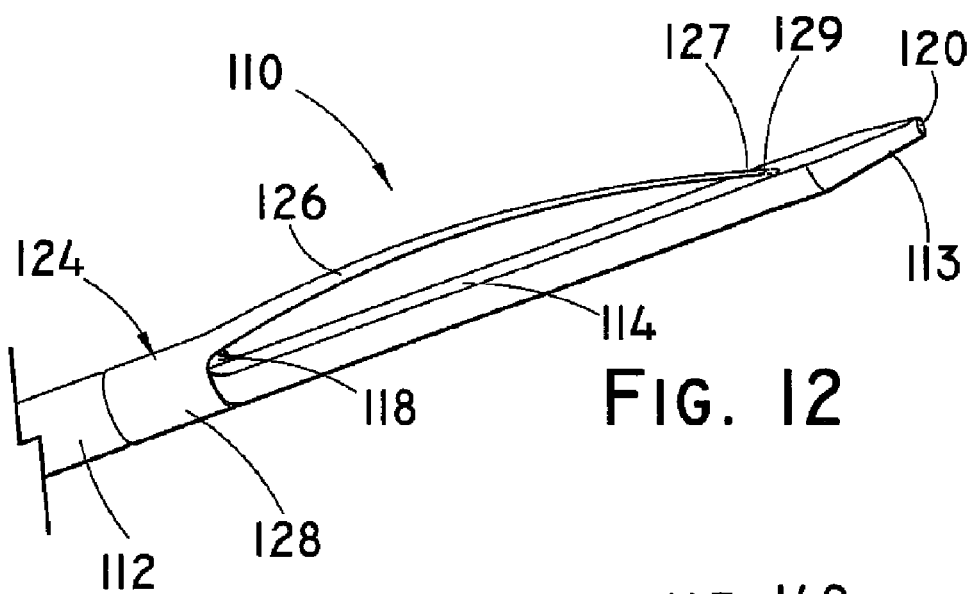
FIG. 12 is a perspective view of the distal portion of another embodiment of a catheter assembly according to the present invention.

For purposes of promoting an understanding of the present invention, reference will now be made to the embodiments illustrated in the drawings, and specific language will be used to describe the same. The figures are not all drawn to the same scale to avoid obscuring the details of the finer structures. The following detailed description of the preferred embodiments will make clear the preferred arrangement, size relationships and manner of using the components shown herein.

The present invention is directed to a multi-lumen catheter assembly for use in the transport of bodily fluids for treatment external of the body, referred to in the art as "extracorporeal" treatment. The fluids are transported from the body through an aspiration lumen in the catheter, and are thereafter transported to an instrument for extracorporeal treatment. The treated fluids are then returned to the body through an infusion lumen in the catheter.

Those skilled in the art will appreciate that the catheter assembly described herein is suitable for multiple uses involving inflow and outflow of bodily fluids. For convenience, the invention will be primarily described hereinafter with reference to one of its intended uses, namely as a hemodialysis catheter assembly for use in the extracorporeal treatment of blood. The catheter assembly enables blood inflow without disruption, and blood return without hemolysis. In addition to hemodialysis, the catheter assembly can be used for other extracorporeal fluid treatments in which a body fluid is withdrawn from the body, subjected to a treatment process, and thereafter returned to the body. Pheresis and hemofiltration are non-limiting examples of such procedures.

In the following discussion, the terms "proximal" and "distal" will be used to describe the axial ends of the catheter assembly, as well as the axial ends of various component features. The "proximal" end refers to the end of the catheter assembly (or component) that is closest to the operator during use of the assembly. The "distal" end refers to the end of the assembly (or component) that is initially inserted into the patient, or that is closest to the patient during use.

FIG. 1 is a perspective view of a multi-lumen catheter assembly 10, according to one embodiment of the present invention. Multi-lumen catheter assembly 10 includes a catheter body 12. Catheter body 12 comprises an outer elongated tubular member formed of a conventional polymer commonly used for such purposes in medical catheters, such as radiopaque polyurethane. Other conventional materials used for such purposes in the medical device art may be substituted. Non-limiting examples of such materials include silicone, nylon and polyethylene. Catheter body 12 has a proximal end 14, a tapered distal end 16, and includes lumens 18, 20 extending at least partially therethrough (FIGS. 3-5).

In the preferred embodiment shown, catheter assembly 10 includes a bifurcated fitting, such as manifold 30. Manifold 30 may be provided with conventional suture wings 31 if desired. Extension tubes 32, 34 extend in the proximal direction from manifold 30. Extension tubes 32, 34 comprise generally flexible polymers commonly used for such purposes in the medical device art, such as polyurethane, PVC and silicone. Catheter body 12 is received in manifold 30 in conventional fashion, such as by insert molding catheter body proximal end 14 in a suitably-sized channel in manifold 30. Extension tube 32 communicates with fluid aspiration lumen 18 in catheter body 12 for receiving fluid withdrawn from a body vessel in the patient. A luer lock or other suitable connector 36 is fitted onto the proximal end of extension tube 32 in conventional fashion. During use of catheter assembly 10, connector 36 engages in mating relationship with a connector associated with an ingress opening of a treatment instrument 50, such as a dialyzer, for establishing a flow path of blood to the dialyzer. Extension tube 34 communicates with blood infusion lumen 20 in catheter body 12. A luer lock or other suitable connector 38 is fitted onto the proximal end of extension tube 34. During use of catheter assembly 10, connector 38 engages in mating relationship with a connector associated with an egress opening of dialyzer 50 for receiving treated blood from the dialyzer. Dialyzer 50 and its ingress and egress openings are shown schematically in FIG. 1. Conventional clamps 37, 39 may be provided for selectively controlling the flow of blood between the dialyzer and the catheter body.

Catheter body 12 may be further understood upon viewing FIGS. 2-5. FIG. 2 is an enlarged side view of the distal portion of catheter assembly 10. FIG. 3 is a longitudinal sectional view of the portion of the catheter assembly shown in FIG. 2. FIG. 3A is a variation of FIG. 3 wherein a toggle is substituted for the hook in FIG. 3. FIG. 4 is a transverse sectional view of the catheter assembly taken along line 4-4 of FIG. 1. FIG. 5 is a transverse sectional view of the catheter assembly taken along line 5-5 of FIG. 1.

Lumens 18, 20 of catheter body 12 are separated by a septum 22. In the preferred embodiment shown, lumen 18 is the aspiration lumen and lumen 20 is the infusion lumen. Fluid aspiration lumen 18 extends from aspiration port 19 to the proximal end of catheter body 12. As best shown in FIGS. 2 and 3, a distal portion of catheter body 12 is cut away a defined distance of, for example, about 30 mm from the most proximal (or nearest) port. To ensure ease of insertion, port 19 is preferably cut at an oblique angle, as shown in FIGS. 2 and 3.

Fluid infusion lumen 20 extends from infusion port 21 to the proximal end of catheter body 12. Preferably, infusion port 21 comprises an open distal tip of catheter body 12. One or more side ports 23 may be provided along the length of catheter body 12 in communication with infusion lumen 20. When present, side ports 23 provide extra surface area for infusion of treated blood into the vessel in addition to infusion port 21. In the preferred embodiment shown, aspiration port 19 is positioned proximal to infusion port 21 and side ports 23 along the length of catheter body 12. This arrangement is preferred, but not crucial to the invention. Positioning the aspiration port proximal to the infusion port and side ports assures that the majority of the blood that is aspirated through the aspiration port is not the same blood that has previously been cleansed and returned to the vessel through the infusion port.

A centering structure, such as double bail 42, is provided at the distal end of catheter body 12. In the embodiment shown, double bail 42 comprises a springy, resilient wire, such as spring tempered stainless steel round wire or nitinol round wire, that is initially bent to the general configuration shown in FIG. 6. As shown in FIG. 6, wire 42 is preferably bent in a manner such that bail members 42A and 42B, and a loop 43A are defined thereby. The presence of loop 43A provides flexibility to the bent structure. Although the loop structure of loop 43A is preferred, double bail 42 can also be configured to simply comprise spring end 43B, as shown in FIG. 6A. Each of bail members 42A and 42B is preferably bent at an end thereof to include a hook-like structure, designated herein as hooks 44, 45. Those skilled in the art will appreciate that other structures can perform the same function as hooks 44, 45 of maintaining a bail member within a generally fixed position in a catheter, and any such structures can be substituted for the hooks. One preferred alternative structure comprises the use of toggles. One such toggle, toggle 44A, is shown in FIG. 3A.

As best illustrated in FIGS. 1-3, double bail 42 is arranged in catheter body 12 such that loop 43A of the double bait is received in lumen 18. Each one of hooks 44, 45 is received in a respective opening 46, 47 formed in the distal portion of the catheter body, and preferably in septum 22. When double bail 42 is arranged in this manner, bail members 42A and 42B span the length of septum between aspiration port 19 and openings 46, 47. Due to the elasticity or shape memory of the wire of double bail 42, bail members 42A, 42B bow outwardly to the general configuration shown in FIGS. 1-3. By bowing outwardly in this manner, bail members 42A, 42B act to increase the effective radial diameter of catheter body 12 between aspiration port 19 and septum openings 46, 47. Increasing the effective radial diameter in this manner maximizes the spacing between the vessel and the aspiration port, while at the same time minimizing the possibility of port occlusion. The resulting configuration subjects the aspiration port to a flow path substantially unhindered by a vessel wall in close proximity.

The axial ends of bail members 42A, 42B are fixed in openings 46, 47 by way of hooks 44, 45. Loop 43A, on the other hand, is freely movable within lumen 18. The bail members are dimensioned with respect to the lumen 18 and openings 46, 47 such that the loop can retract a certain distance within the lumen, and yet will not pop out of the lumen. As a result, the radial outward extension of bail members 42A, 42B may be selectively transitioned between the outwardly bowed configuration shown in FIGS. 1-3, and a low profile configuration wherein double bail 42 does not extend outwardly beyond the outer diameter of catheter body 12.

In a preferred embodiment, an introducer sheath 53 may be provided over the distal end of catheter assembly 10. In FIG. 7, introducer sheath 53 is shown partially extended in the proximal direction, such that it covers about one-half of the length of the bail members. When sheath 53 is fully extended in the proximal direction, it covers all, or substantially all, of bail members 42A, 42B. In this event, loop 43A is urged in a proximal direction within lumen 18, and bail members 42A, 42B are radially compressed within the catheter assembly. The bail members remain in this compressed configuration as long as they remain covered by the sheath.

In the non-limiting embodiment shown in FIG. 7, sheath 53 comprises a splittable structure having an elongated body 54 that tapers to a distal end 59. Distal end 59 is dimensioned for insertion into the body vessel. Elongated sheath body 54 is dimensioned to receive the distal end of catheter body 12 therein in a snugly-fitting relationship. A pair of ears 55, 56 is provided, which ears may include graspable knobs 57, 58 for use in splitting the elongated body 54. Splittable introducer sheaths are well known in the medical arts, and a skilled artisan is well aware of the manner of use and splitting of such sheaths. Such sheaths are commercially available e.g., from Cook Incorporated, of Bloomington, Ind., as PEEL-AWAY® introducers.

During one mode of use of catheter assembly 10, the leading (distal) end 59 of introducer sheath 53 is inserted into the vessel. Preferably, the catheter assembly and sheath are introduced into the vessel over a wire guide that has previously been positioned in the vessel by conventional means, such as the well-known Seldinger technique. Following insertion of the catheter assembly and sheath, the wire guide is removed. The sheath is thereafter removed by grasping and pulling the knobs in an outward direction and peeling the sides of the sheath in well-known fashion, leaving the leading (distal) end of the catheter assembly in position in the vessel.

Although it is preferred to introduce the catheter assembly with the use of an introducer sheath, such as splittable sheath 53, this is not required. The use of an introducer device is not always necessary, and in some occasions the catheter assembly can be successfully introduced without the use of such a sheath or other device. Those skilled in the art will appreciate that a generally radial force is applied to the bails upon insertion into a vessel by the adjacent tissue at the insertion site. This force will cause the bails to collapse upon insertion, in the same manner as the force of an introducer sheath covering the bails. Upon entering the vessel, the force is removed, and the bails expand to the radial configuration described. The same principle applies during removal of the catheter assembly from the vessel.

The centering structure need not necessarily comprise a double bail wire 42 as shown in the previous embodiment. Rather, any structure that is capable of selectively transitioning between a radial extension and a low profile configuration may be substituted. FIGS. 8 and 9 illustrate the distal end of one alternative embodiment of a catheter assembly 70. The proximal end of catheter assembly 70 may be similar to that shown in FIG. 1. Once again, catheter body 72 comprises an outer elongated tubular member having a proximal end (not shown) and a tapered distal end 74. Aspiration and infusion lumens 82, 84, extend through catheter body 72 as before, and are separated by septum 76. Aspiration port 78 and infusion port 80 are provided as before. One or more side ports 79 may be provided to communicate with the infusion lumen as before.

In this embodiment, the centering structure comprises a generally helical bail 85 at the distal end of catheter body 72. Bail 85 may comprise a wire such as the wire used in double bail 42. A generally hook-like or toggle-like structure 86 is provided at the distal end of bail 85, which hook or toggle is received in opening 77 in the wall of septum 76. The bail is wound around the distal portion of catheter body 72 in generally helical fashion as shown.

The proximal end 87 of bail 85 is freely received in aspiration lumen 82 in the same manner as bail loop 43A in the previous embodiment. The distal end 89 of bail 85 is substantially affixed to the catheter by the hooks or toggles described, or alternatively by other well-known attachment mechanisms. Non-limiting examples of such attachment mechanism include adhesion, bonding (such as heat bonding), sutures, and the like. Due to the springiness of bail 85, the bail bows outwardly in the manner shown in the figures, thereby increasing the effective radial diameter of catheter body 72. Significant contact between aspiration port 78 and the vessel wall is inhibited, thereby minimizing the possibility of occlusion of the port.

FIGS. 10 and 11 illustrate the distal end of another embodiment of a catheter assembly 90. Once again, the proximal end may be similar to that shown in FIG. 1. Catheter body 92 comprises an outer elongated tubular member having a tapered distal end 94. Aspiration and infusion lumens 102, 104 are separated by septum 96, and an aspiration port 98 and infusion port 100 are provided as before. If desired, one or more side ports 99 may also be provided to communicate with the infusion lumen.

In this embodiment, the centering structure comprises a generally sinusoidal shaped bail 105 at the distal end of catheter body 92. Once again, bail 105 comprises a generally resilient wire, such as the wire described previously. A generally hook-like, toggle-like or other suitable structure 106 is provided at the distal end 107 of bail 105, which hook is received in opening 97 in the wall of septum 96. The proximal end 108 of bail 105 is freely received in aspiration lumen 102.

Although the centering structures have been described herein as formed from wire, such structures may alternatively be formed from other components that may be adapted to function in like manner. For example, a centering structure can be formed from a cannula or small tubular structure. The cannula may be formed from a metal or a metal alloy, such as stainless steel or nitinol, that is cut in a conventional manner, such as via a laser cut, to define a centering element. Those skilled in the art will appreciate that other alternatives are possible, such as a small diameter plastic tube or strip. These structures can be shaped, such as via heat/steam, to have any of the shapes described.

FIG. 12 is a perspective view of the distal portion of another embodiment of a catheter assembly 110 according to the present invention. Catheter assembly 110 includes elongated catheter body 112 having a tapered distal end 113. The proximal end of catheter assembly 110 is conventional, and need not be further described to attain an understanding of the invention. Catheter body 112 has aspiration and infusion lumens (not shown) extending through the catheter body in the same manner as before. The lumens are separated by a septum 114, and an aspiration port 118 and an infusion port 120 for the respective lumens are provided as before If desired, one or more side ports (not shown) may also be provided to communicate with the infusion lumen.

A centering structure is formed from a cannula or small metal tube. In the embodiment of FIG. 12, cannula 124 is cut, such as via a laser cut, to define a spine 126 at a distal portion thereof. Laser cutting a substrate, such as a cannula, to form a spine or similar structure is a well known process, and a skilled artisan readily program a computer to cut this, or other, shapes from a cannula. Alternatively, the spine could be formed from a suitably-shaped or cut material, such as metal or metal alloy, and affixed to a main body, such as a cannula, by conventional means such as bonding or adhesion.

Proximal portion 128 of the cannula is sized to snugly fit over catheter body 112, preferably proximal of aspiration port 118. Alternatively, other conventional means, such as adhesion, may be utilized to maintain cannula proximal portion 128 in the position shown on catheter body 112. Spine 126 has a distal end portion 127 that is movably received in a slit, or opening, 129 of septum 114, in a manner that allows longitudinal compliance of the spine (i.e., retraction of spine distal end portion 127 into slit 129) upon exposure of the spine to an external radially-inwardly directed force. Upon removal of the external force, resilient spine 126 assumes the radial extension shown in FIG. 12. Spine 126 is provided with sufficient length such that spine distal end portion 127 will not fully come out of the slit as the force is removed and spine extends radially as shown.

Figure 13:
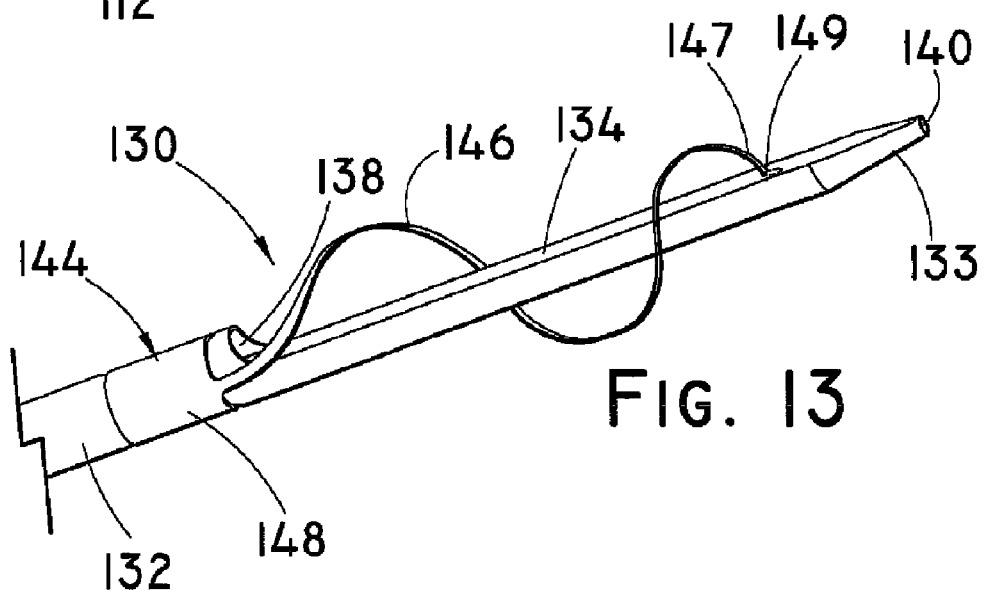
FIG. 13 is a perspective view of the distal portion of yet another embodiment of a catheter assembly according to the present invention.
Figure 14:
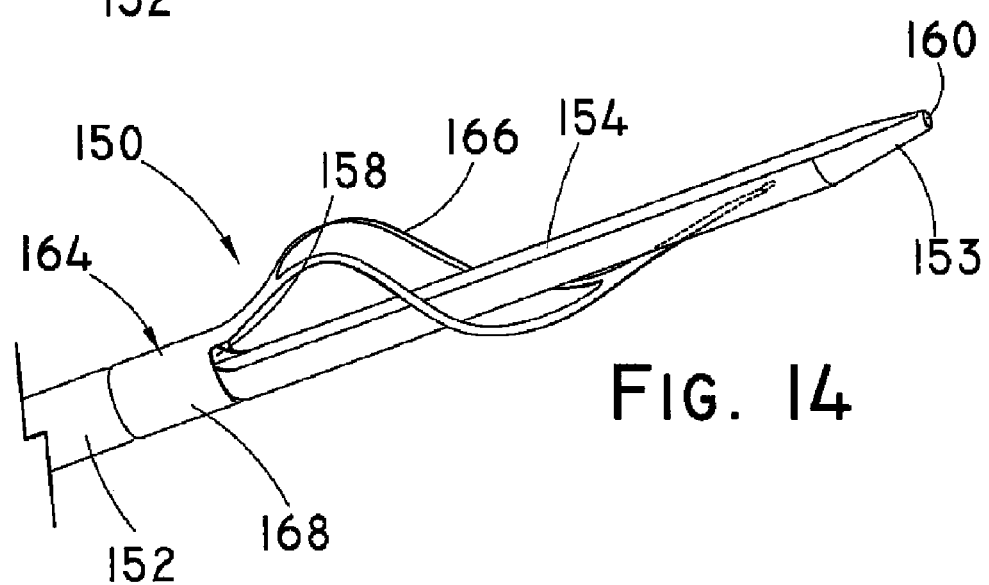
FIG. 14 is a perspective view of the distal portion of still another embodiment of a catheter assembly according to the present invention.

FIGS. 13 and 14 show additional variations of a centering structure formed from a cannula or small metal tube. In FIG. 13, catheter assembly 130 includes elongated catheter body 132 having a tapered distal end 133, and having aspiration and infusion lumens (not shown) as before. The lumens are separated by a septum 134, and an aspiration port 138 and an infusion port 140 are provided as before. Side ports (not shown) may be provided if desired.

In the embodiment of FIG. 13, the cannula 144 is laser cut or otherwise formed to define a helical structure 146 that wraps around catheter body 132, and more particularly, around the exposed portion of septum 134. Proximal portion 148 of the cannula snugly fits over catheter body 132 proximal of aspiration port 138. Helical structure 146 has a distal end portion 147 that is movably received in a slit, or opening, 149 of septum 134, in the same manner as in the embodiment of FIG. 12.

In FIG. 14, catheter assembly 150 includes elongated catheter body 152 having a tapered distal end 153, and having aspiration and infusion lumens (not shown) as before. The lumens are separated by a septum 154, and an aspiration port 158 and an infusion port 160 are provided as before. Side ports (not shown) may be provided if desired. In the embodiment of FIG. 14, the cannula 164 is laser cut to define a looped, or "caged", structure 166 that wraps around catheter body 152, and particularly, around the exposed portion of septum 154. Proximal portion 168 of the cannula snugly fits over catheter body 152 proximal of aspiration port 158. The caged structure 166 has a distal end portion that is movably received in a slit, or opening, (not shown) of catheter body 152, in the same manner as in the embodiments of FIGS. 12 and 13.

The catheter assemblies illustrated in FIGS. 12-14 may be inserted into the body vessel in the same manner as in the previous embodiments. If desired, an introducer sheath, such as the splittable sheath 53 described above, may be utilized for introduction of the catheter assemblies into the vessel.

Those skilled in the art will appreciate that the spine 126, helical structure 146 and caged structure 166 shown in respective FIGS. 12-14 are merely examples of structures that can be provided to space a catheter port, such as the aspiration port described herein, from a vessel wall, and that other structures capable of the same or similar function can be substituted. Those skilled in the art will further appreciate that minor modification can be made to the structures illustrated and/or described herein to accomplish the same or similar function, all such structures and/or modifications being considered within the scope of the invention.

It is therefore intended that the foregoing detailed description be regarded as illustrative rather than limiting, and that it be understood that it is the following claims, including all equivalents, that are intended to define the spirit and scope of this invention.

The invention claimed is:

1. A multi-lumen catheter assembly, comprising:
a catheter body having a plurality of lumens extending therein, said catheter body having an aspiration port in communication with a first lumen for transporting fluid withdrawn from a body vessel, and an infusion port in communication with a second lumen for return of said fluid to said vessel, said infusion port positioned distal of the aspiration port along a length of said catheter body, said catheter body including a septum separating said first and second lumens; and
a flexible member having a first end and a second end, said first end slidably received in said first lumen, said second end engaged with said catheter body septum distal of said aspiration port, said first and second ends of said flexible member defining a length of said septum, said flexible member having a maximal radial extension along said septum length to maintain a spacing between said aspiration port and a wall of said vessel.

2. The multi-lumen catheter assembly of claim 1, wherein said catheter body tapers to an open distal end, said open distal end comprising said infusion port, and wherein said septum extends at least substantially to said infusion port along said catheter body length.

3. The multi-lumen catheter assembly of claim 2, further comprising at least one side port disposed along a length of said elongated member in communication with said infusion lumen for returning treated body fluid into said vessel.

4. The multi-lumen catheter assembly of claim 1, wherein said flexible member defines at least one loop spanning said septum length and extending radially outwardly from said septum.

5. The multi-lumen catheter assembly of claim 1, wherein said flexible member is configured to comprise at least two loops, wherein each of said loops extends radially outwardly from said septum.

6. The multi-lumen catheter assembly of claim 1, wherein said flexible member is wrapped in a generally helical configuration around said catheter body along said spanned septum length.

7. The multi-lumen catheter assembly of claim 1, wherein said flexible member is configured in a generally serpentine configuration along said spanned septum length.

8. The multi-lumen catheter assembly of claim 1, further comprising a removable sheath sized to be received over a distal portion of said catheter body and said flexible member for reducing a radial profile of said flexible member.

9. The multi-lumen catheter assembly of claim 8, wherein said sheath comprises a splittable sheath body.

10. The multi-lumen catheter assembly of claim 1, wherein said catheter body comprises a flexible polymer and said flexible member comprises a wire formed of one of spring tempered stainless steel and nitinol.

11. A multi-lumen catheter assembly, comprising:
an elongated catheter body having a plurality of lumens extending therein, said catheter body having an aspiration port in communication with a first lumen for transporting fluid withdrawn from a body vessel, and an infusion port in communication with a second lumen for return of said fluid to said vessel, wherein said infusion port is positioned distal of the aspiration port along a length of said elongated catheter body, said catheter body including a septum separating said first and second lumens, a length of said septum extending between said aspiration port and said infusion port being uncovered by said catheter body; and
a centering member having a proximal portion disposed along a length of said catheter body proximal of said aspiration port, and having a flexible member extending from said proximal portion in a distal direction along said catheter length, said flexible member spanning said uncovered length of said septum and configured to maintain a spacing between said aspiration port and a wall of said body vessel; wherein said proximal portion of said centering member comprises a cannula securely fitted about a surface of said body.

12. The multi-lumen catheter assembly of claim 11, wherein said catheter body includes an opening distal of said aspiration port, and wherein a distal end of said flexible member is movably received in said opening.

13. The multi-lumen catheter assembly of claim 11, wherein said centering member comprises a cannula having said flexible member cut from a distal portion thereof.

14. The multi-lumen catheter assembly of claim 13, wherein said flexible member comprises one of a spine, a helix, and a cage.

15. A multi-lumen catheter assembly, comprising:
a catheter body having a plurality of lumens extending therein, said catheter body having an aspiration port in communication with a first lumen for transporting fluid withdrawn from a body vessel, and an infusion port in communication with a second lumen for return of said fluid to said vessel, said infusion port positioned distal of the aspiration port along a length of said catheter body, said catheter body including a septum separating said first and second lumens; and
a flexible member having a first end and a second end, said first end slidably received in said first lumen, said second end engaged with said catheter body septum distal of said aspiration port, said flexible member spanning a length of said septum between said first end and said second end, said flexible member structured and arranged to maintain a spacing between said aspiration port and a wall of said vessel, wherein said flexible member comprises a double bail, said double bail comprising a pair of bail members and a connector member joining said bail members at said first end, said connector member slidably received in said first lumen.

16. The multi-lumen catheter assembly of claim 15, wherein said connector member comprises a loop.

* * * * *